United States Patent
Wang et al.

(10) Patent No.: US 9,459,217 B2
(45) Date of Patent: Oct. 4, 2016

(54) HIGH-RESOLUTION COMPUTED TOMOGRAPHY

(71) Applicant: Illinois Tool Works, Inc., Glenview, IL (US)

(72) Inventors: Yuxin Wang, Palatine, IL (US); Joshua A. Sharpe, New Brighton, MN (US); Joseph Schlecht, Edina, MN (US); Eric Ferley, Rogers, MN (US); Julien Noel, Puteaux (FR)

(73) Assignee: Illinois Tool Works, Inc., Glenview, IL (US)

( * ) Notice: Subject to any disclaimer, the term of this patent is extended or adjusted under 35 U.S.C. 154(b) by 0 days.

(21) Appl. No.: 14/781,541

(22) PCT Filed: Apr. 2, 2014

(86) PCT No.: PCT/US2014/032670
§ 371 (c)(1),
(2) Date: Sep. 30, 2015

(87) PCT Pub. No.: WO2014/168796
PCT Pub. Date: Oct. 16, 2014

(65) Prior Publication Data
US 2016/0047759 A1   Feb. 18, 2016

Related U.S. Application Data

(60) Provisional application No. 61/811,151, filed on Apr. 12, 2013.

(51) Int. Cl.
*G01N 23/04*    (2006.01)
*G06T 3/40*    (2006.01)

(52) U.S. Cl.
CPC ........... *G01N 23/046* (2013.01); *G06T 3/4069* (2013.01); *G01N 2223/419* (2013.01); *G01N 2223/42* (2013.01); *G01N 2223/427* (2013.01)

(58) Field of Classification Search
CPC ...... G01N 23/04; G01N 23/06; A61B 6/547; A61B 6/469; A61B 6/5205; A61B 6/4233; G06T 2207/10116; G06T 2207/10016
See application file for complete search history.

(56) References Cited

U.S. PATENT DOCUMENTS

| 4,907,152 A | 3/1990 | Lempriere |
| 5,340,988 A | 8/1994 | Kingsley et al. |

(Continued)

FOREIGN PATENT DOCUMENTS

| EP | 1387321 A2 | 2/2004 |
| EP | 2196797 A1 | 6/2010 |

(Continued)

OTHER PUBLICATIONS

Krejci et al., "Enhancement of Spatial Resolution of Roentgenographic Methods Using Deconvolution," 2008 IEEE Nuclear Science Symposium Conference Record, M06-315, Oct. 19-25, 2008, pp. 4124-4129.

(Continued)

*Primary Examiner* — Hoon Song
(74) *Attorney, Agent, or Firm* — Shumaker & Sieffert, P.A.

(57) ABSTRACT

An x-ray imaging system (10), such as a X-ray computerized tomographic system, may acquire a series of radiographs at different detector positions along a first translation axis or a second translation axis parallel to orientation directions of detector pixels of a radiation detector (14). In a first embodiment, the different detector positions may be separated by a distance less than a linear size of the radiation detector (14) along the first translation axis or the second translation axis, respectively. The radiographs may be assembled into a radiograph larger than each radiograph in the series of radiographs, resulting in image stitching. In a second embodiment, the different detector positions may be separated by a distance less than a pixel size of the radiation detector (14), also referred as sub-pixel shifting of the detector. The radiographs may be assembled to form a radiograph with a higher resolution than the acquired radiographs, resulting in superresolution.

31 Claims, 9 Drawing Sheets

(56) References Cited

U.S. PATENT DOCUMENTS

| | | | |
|---|---|---|---|
| 7,136,454 B2 | 11/2006 | Gerndt et al. | |
| 7,199,357 B1 | 4/2007 | Oldham et al. | |
| 8,229,061 B2 | 7/2012 | Hanke et al. | |
| 8,299,413 B2 | 10/2012 | Vogt et al. | |
| 8,542,793 B1 * | 9/2013 | Jin | G01N 23/046 378/4 |
| 2003/0007601 A1 * | 1/2003 | Jaffray | A61B 6/032 378/65 |
| 2009/0207964 A1 | 8/2009 | Pack | |
| 2010/0303208 A1 | 12/2010 | Baruth et al. | |
| 2011/0075910 A1 | 3/2011 | Kanagawa et al. | |
| 2012/0051514 A1 | 3/2012 | Sims et al. | |
| 2014/0072095 A1 * | 3/2014 | Feser | G01N 23/2206 378/4 |
| 2016/0054239 A1 | 2/2016 | Schlecht et al. | |

FOREIGN PATENT DOCUMENTS

| | | |
|---|---|---|
| WO | 03015634 A1 | 2/2003 |
| WO | 2009153789 A1 | 12/2009 |
| WO | 2012147081 A1 | 11/2012 |

OTHER PUBLICATIONS

Kyrieleis et al., "Image stitching strategies for tomographic imaging of large objects at high resolution at synchrotron sources," Nuclear Instruments and Methods in Physics Research A, vol. 607, Jun. 21, 2009, pp. 677-684.

Thim et al., "Realizing increased sub-pixel spatial resolution in X-ray imaging using displaced multiple images," Nuclear Instruments and Methods in Physics Research A, vol. 633, Jul. 3, 2010, pp. S247-S249.

Wypych et al., "System for Inspection of Large High-Resolution Radiography Datasets," 2011 IEEE Aerospace Conference, Mar. 5-12, 2011, pp. 1-9.

International Search Report and Written Opinion of International Application No. PCT/US2014/032670, mailed Sep. 18, 2014, 19 pp.

International Preliminary Report on Patentability from International Application No. PCT/US2014/032670, mailed Jul. 2, 2015, 11 pp.

Invitation to Pay Additional Fees from International Application No. PCT/US2014/032670, dated Jul. 18, 2014, 7 pp.

Invitation to Pay Additional Fees from International Application No. PCT/US2014/032670, dated Mar. 19, 2015, 3 pp.

Response to Invitation to Pay Additional Fees dated Jul. 18, 2014, from International Application No. PCT/US2014/032670, dated Aug. 14, 2014, 4 pp.

Response to Invitation to Pay Additional Fees dated Mar. 19, 2015, from International Application No. PCT/US2014/032670, dated Apr. 16, 2015, 4 pp.

Response to Written Opinion mailed Sep. 18, 2014, from International Application No. PCT/US2014/032670, dated Feb. 9, 2015, 25 pp.

Bruandet et al., "Improving x-ray image resolution using subpixel shifts of the detector," SPIE Proceedings, vol. 3661, Medical Imaging 1999: Image Processing, Feb. 20, 1999, 2 pages. (Abstract Only).

Kalender et al., "flat-detector computed tomography (FD-CT)," Computer Tomography, Eur Radiol, vol. 17, Springer-Verlag, Jun. 23, 2007, pp. 2767-2779.

Katsevich et al., "Theoretically Exact Filtered Backprojection-Type Inversion Algorithm for Spiral CT," SIAM Journal on Applied Mathematics, vol. 62, No. 6, Jul. 3, 2002, pp. 2012-2026.

Extended Search Report from counterpart European Application No. 16150940.1, dated May 25, 2016, 4 pp.

Varslot et al., "Fast high-resolution micro-CT with exact reconstruction methods," Developments in X-Ray Tomography VII, Proceedings of SPIE, vol. 7804, Sep. 20, 2010, 10 pp.

\* cited by examiner

HIGH-RESOLUTION COMPUTED TOMOGRAPHY

This application is a National Stage Entry under 35 U.S.C. §371 of International Application No. PCT/US2014/032670 filed Apr. 2, 2014, which claims the benefit of U.S. Provisional Application No. 61/811,151, filed Apr. 12, 2013; the entire content of each of which is incorporated herein by reference.

TECHNICAL FIELD

This disclosure relates to x-ray digital radiography and computed tomography.

BACKGROUND

X-ray digital radiography (DR) is a commonly used non-invasive and non-destructive imaging technique using digital x-ray detectors, such as flat-panel detectors, charge-coupled device (CCD) cameras, or complementary metal-oxide-semiconductor (CMOS) cameras, or linear diode arrays (LDAs). X-ray computed tomography (CT) is a procedure that uses computer-processed x-rays radiographs acquired at different view angles to produce 3D images of an object. A tomographic image of an object is an image of a conceptually two-dimensional "slice" of the object. A computing device may use the tomographic images of the object to generate a 3-dimensional image of the object. X-ray CT may be used for industrial purposes to conduct non-destructive evaluation of objects.

SUMMARY

In general, this disclosure relates to industrial x-ray radiography, computed tomography (CT) and non-destructive evaluation (NDE). This disclosure describes an apparatus and image acquisition method that may expand an effective field of view of two-dimensional (2D) x-ray radiography and three-dimensional (3D) x-ray CT techniques beyond a physical size of a detector used in the apparatus, as well as increase the effective image resolution beyond the pixel size. The techniques of this disclosure provide an instrumentation design, user control mechanism, and software algorithm for the apparatus. The apparatus may be used for NDE of naturally occurring objects, such as rock core samples as well as manufactured components and systems, such as metal casts, engine components, and complete engine units. The apparatus may comprise an x-ray source, a radiation detector, and a sample manipulator, each with associated motion control systems. The sample manipulator may position samples so that radiographs can be obtained at different positions and viewing angles.

In one example, this disclosure describes an x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; and an image acquisition system configured to: acquire a series of radiographs at different detector positions along one or both of the translation axes, the different detector positions separated by a distance finer than a pixel size of the radiation detector, and assemble the radiographs to form a composite radiograph with finer resolution than the acquired radiographs.

In another example, this disclosure describes an x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; and an image acquisition system configured to: acquire a series of radiographs at different detector positions along one or both of the translation axes, the different detector positions separated by a distance less than a linear size of the radiation detector along the respective translation axis; and assemble the radiographs into a composite radiograph larger than each radiograph in the series of radiographs.

In another example, this disclosure describes a method comprising acquiring a series of radiographs at different detector positions along a first or a second translation axis parallel to orientation directions of detector pixels of a radiation detector, the different detector positions separated by a distance finer than a pixel size of the radiation detector, the radiation detector having a plane arranged perpendicular to an emission direction of an x-ray beam emitted by an x-ray generator, wherein a first translation stage and a second translation stage carry the radiation detector, wherein the first and second translation stages are configured to move the radiation detector along the first and second translation axes; and assembling the radiographs to form a composite radiograph with finer resolution than the acquired radiographs.

In another example, this disclosure describes a method comprising: acquiring a series of radiographs at different detector positions along a first or a second translation axis parallel to orientation directions of detector pixels of a radiation detector, the different detector positions separated by a distance less than a linear size of the radiation detector along the first translation axis or the second translation axis, respectively, wherein the radiation detector has a plane arranged perpendicular to an emission direction of an x-ray beam emitted by an x-ray generator, a first translation stage and a second translation stage carry the radiation detector, and the first and second translation stages are configured to move the radiation detector along the first and second translation axes; and assembling the radiographs into a composite radiograph larger than each radiograph in the series of radiographs.

In another example, this disclosure describes a non-transitory computer-readable data storage medium having instructions stored thereon that, when executed, cause a computing system to: acquire a series of radiographs at different detector positions along a first translation axis or a second translation axis parallel to orientation directions of detector pixels of a radiation detector, the different detector positions separated by a distance finer than a pixel size of the radiation detector, the radiation detector having a plane arranged perpendicular to an emission direction of an x-ray beam emitted by an x-ray generator, wherein a first translation stage and a second translation stage carry the radiation detector, wherein the first and second translation stages are configured to move the radiation detector along the first and second translation axes; and assemble the radiographs to form a composite radiograph with finer resolution than the acquired radiographs.

In another example, this disclosure describes a non-transitory computer-readable data storage medium having instructions stored thereon that, when executed, cause a computing system to: acquire a series of radiographs at different detector positions along a first translation axis or a second translation axis parallel to orientation directions of detector pixels of a radiation detector, the different detector positions separated by a distance less than a linear size of the radiation detector along the first translation axis or the second translation axis, respectively, wherein the radiation detector has a plane arranged perpendicular to an emission direction of an x-ray beam emitted by an x-ray generator, a first translation stage and a second translation stage carry the radiation detector, and the first and second translation stages are configured to move the radiation detector along the first and second translation axes; and assemble the radiographs into a composite radiograph larger than each radiograph in the series of radiographs.

The details of one or more examples are set forth in the accompanying drawings and the description below. Other features, objects, and advantages will be apparent from the description, drawings, and claims.

DETAILED DESCRIPTION

Figure 1:
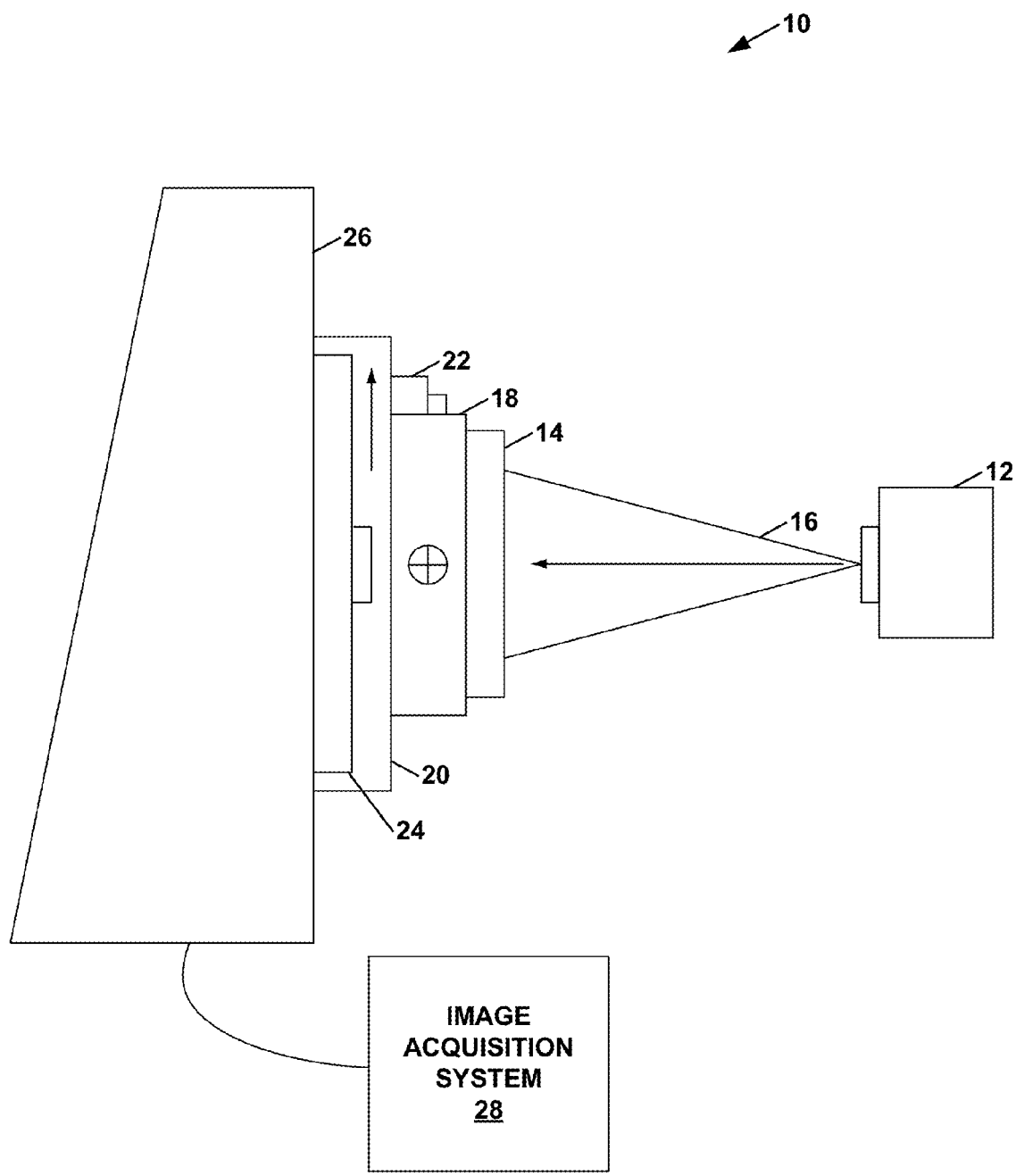
FIG. 1 is a schematic drawing of an example instrumental setup, in accordance with one or more techniques of this disclosure.

X-ray radiography and computed tomography (CT) are commonly used methods of non-invasively or non-destructively obtaining three-dimensional structures in medical imaging and industrial non-destructive evaluation (NDE). One or more example techniques of this disclosure relate to industrial applications of x-ray CT. FIG. 1 is a schematic drawing of an example instrumental setup, in accordance with one or more techniques of this disclosure. As shown in the example of FIG. 1, an industrial CT system 10 may include an x-ray source 12 and a radiation detector 14. X-ray source 12 may emit an x-ray beam 16. Hence, in some instances, this disclosure may refer to x-ray source 12 or similar devices as "x-ray generators." In some examples, x-ray beam 16 may be cone-shaped. In other examples, x-ray beam 16 may be fan-shaped. In some examples, x-ray source 12 generates x-rays with an energy range of 20 keV to 600 keV. In other examples, x-ray source 12 may generate x-rays in other energy ranges.

Samples may be mounted on a manipulator. In industrial CT system 10, the manipulator may include a rotary stage (i.e., a rotation stage) with an axis of rotation perpendicular to the x-ray beam axis. The rotary stage may be configured to carry and rotate a sample and may be disposed between x-ray source 12 (i.e., an x-ray generator) and radiation detector 14 (i.e., a radiation detector). Consequently, radiographs may be acquired at different projection angles as the sample is rotated in x-ray beam 16. Thus, in some examples where the manipulator includes a rotation stage, a computing system of industrial CT system 10 may acquire radiographs at different detector positions for different rotation angles and may process the radiographs to assemble the radiographs into a 3-dimensional radiograph of the sample.

Radiation detector 14 may include a flat panel x-ray detector (FPD) shown in the example of FIG. 1. In other examples, radiation detector 14 may include a lens-coupled scintillation detector, a linear diode array (LDA), or another type of x-ray detector. A FPD may include a layer of scintillation material, such as Cesium Iodide fabricated on amorphous silicon on a glass detector array. The scintillator layer absorbs x-rays and emits visible light photons that are, in turn, detected by a solid state detector. The detector pixel size may range from tens to hundreds of micrometers. In some examples where radiation detector 14 comprises a flat-panel x-ray detector, the pixel size of radiation detector 14 may be in the range of 25 micrometers to 250 micrometers. In some examples, the pixel size of radiation detector 14 may be in the range of approximately 25 micrometers to approximately 250 micrometers. Furthermore, the field of view of common commercial FPDs may range from approximately 100 mm to 500 mm. Commercial FPDs may be used in applications requiring large fields of view.

High-resolution applications may require lens-coupled detectors that use an optical tens to relay emitted visible light to a detector, such as a charge-coupled device (CCD) or a complementary metal-oxide-semiconductor (CMOS) detector. In some examples, the lens may provide magnification in the range of 1× to 100×, thus making the effective pixel size between 0.1 to 20 micrometers. In some examples where radiation detector 14 comprises a lens-coupled detector, the pixel size of radiation detector 14 is in a range of 0.1 micrometers to 10 micrometers. Furthermore, in some examples where radiation detector 14 comprises a lens-coupled detector, the field of view may range from 0.2 mm to 25 mm.

With both types of detectors (e.g., FPDs and lens-coupled scintillation detectors), there may be a compromise between image resolution and field of view. Furthermore, in some applications, a user may wish to expand the field of view beyond the detector's physical size or increase resolution beyond what the pixel size directly supports. The techniques of this disclosure describe instrument designs, image acquisition methods, and computer algorithms to incorporate precise detector motion system to accomplish these two conflicting goals (i.e., increased image resolution and increased field of view).

In accordance with one or more example techniques of this disclosure, an x-ray digital radiography (DR) or CT system includes a precise motion system in a detector system so that the detector system (including radiation detector 14) can translate in x-ray beam 16 in directions perpendicular to a principal axis of x-ray beam 16 and along the rows and columns of pixels of radiation detector 14 (i.e., an x-ray detector). This may achieve one or more objectives, such as the following two objectives. First, by acquiring radiographs at different two or more positions each separated by intervals greater than (e.g., much greater than) the pixel size of radiation detector 14 but less than the detector size, radiation detector 14 may cover a larger area than the physical size of radiation detector 14. These digital radiographs can then be numerically "stitched" together to form a composite radiograph with a greater field of view. Second, by acquiring radiographs when radiation detector 14 is at two or more positions separated by intervals smaller than the pixel size, a sub-pixel size sampling effect may be achieved. This technique, in certain optical configurations and with certain types of samples, can be used to generate composite radiographs with finer resolution. These two techniques can be combined in practical use to significantly increase either or both the imaging field of view and the resolution. Furthermore, these two techniques can further be combined with both conventional volumetric CT and spiral CT techniques to increase the 3-dimensional (3D) reconstructed volume and its resolution.

In a projection-type x-ray radiography and CT system, such as industrial CT system 10 of FIG. 1, the optical resolution may be determined by the size of the x-ray source (e.g., x-ray generator 12), as well as the x-ray detector (e.g., radiation detector 14) which serves to sample and record the x-ray image formed upon it. Under certain imaging conditions, the actual image may contain features finer than the detector pixel size. For example, if industrial CT system 10 of FIG. 1 has a 50 μm x-ray source size in a 2× magnification geometry, industrial CT system 10 may form images on the detector plane with a minimum feature size of 50 μm. When using flat panel detectors with 200 μm pixel size, the x-ray image is not adequately sampled, and sub-pixel sampling may be required to achieve a maximum possible resolution. This may be achieved by either using a sub-pixel sized mask or translating the detector by sub-pixel intervals. The latter method (i.e., translating the detector by sub-pixel intervals) may be advantageous in some situations because the latter method may make use of existing detector motion stages without the need of additional hardware. Translating the sample may not achieve the same effect as translating the radiation detector because translating the sample may alter the imaging geometry.

Industrial CT system 10 of FIG. 1 may overcome one or more of the aforementioned shortcomings. In the example of FIG. 1, industrial CT system 10 comprises an x translation stage 18 and a y translation stage 20. x translation stage 18 and y translation stage 20 may be configured to move radiation detector 14 along translation axes (e.g., x and y translation axes) parallel to orientation directions or detector pixels of radiation detector 14. Thus, industrial CT system 10 may comprise a two-dimensional pixelated area radiation detector 14 with its plane arranged perpendicular to the emission direction of x-ray beam 16 (i.e., the beam axis of x-ray beam 16), and carried on two independent translation stages with each axis parallel to the orientation of the detector pixels. Although x does not necessarily correspond to a horizontal direction and y does not necessarily correspond to a vertical direction, this disclosure may also refer to x translation stage 18 as horizontal translation stage 18 and may refer to y translation stage 24 as vertical translation stage 24.

Furthermore, industrial CT system 10 may comprise an x stage linear encoder 22 and a y stage linear encoder 24. The "x" and "y" dimensions may be orthogonal, and in some cases may refer to horizontal and vertical dimensions. However, x does not necessarily correspond to a horizontal direction and y does not necessarily correspond to a vertical direction. Thus, although this disclosure may also refer to x stage linear encoder 22 as horizontal stage linear encoder 22 and may refer to y stage linear encoder 24 as vertical stage linear encoder 24, the techniques may be extended to other dimensions which may or may not be orthogonal. x stage linear encoder 22 and y stage linear encoder 24 are two independent linear encoders with resolutions finer than one quarter of the detector pixel size (i.e., the size of pixels of radiation detector 14). x stage linear encoder 22 and y stage linear encoder 24 may be arranged in parallel to the two translation stages (i.e., x translation stage 18 and y translation stage 22). x stage linear encoder 22 and y stage linear encoder 24 are driven by the respective translation stages to provide direct measurement of displacement of the translation stages. In the example of FIG. 1, x translation stage 18, y translation stage 20, x stage linear encoder 22 and y stage linear encoder 24 are coupled to and supported by a detector mounting frame 26. In some instances, image acquisition system 28 may assemble radiographs using a measurement of displacement of x stage linear encoder 22 and y stage linear encoder 24. For instance, image acquisition system 28 may use the measurements to determine how to interlace the pixels of radiographs to assemble a higher resolution radiograph and/or a larger sized radiograph (i.e., a composite radiograph).

Industrial CT system 10 also comprises an image acquisition system 28. Image acquisition system 28 may comprise a computing system. Example types of computing systems may include personal computers, server computers, mainframe computers, laptop computers, special-purpose computers, and so on. Image acquisition system 28 may implement a computer-controlled image acquisition procedure comprising (e.g., consisting of) acquiring a series of images at different detector positions along one or both axes separated by a distance finer than the detector pixel size. The computer-controlled image acquisition procedure may use a computer program to assemble the images in an interlaced fashion to form a finer resolution image.

Figure 2:
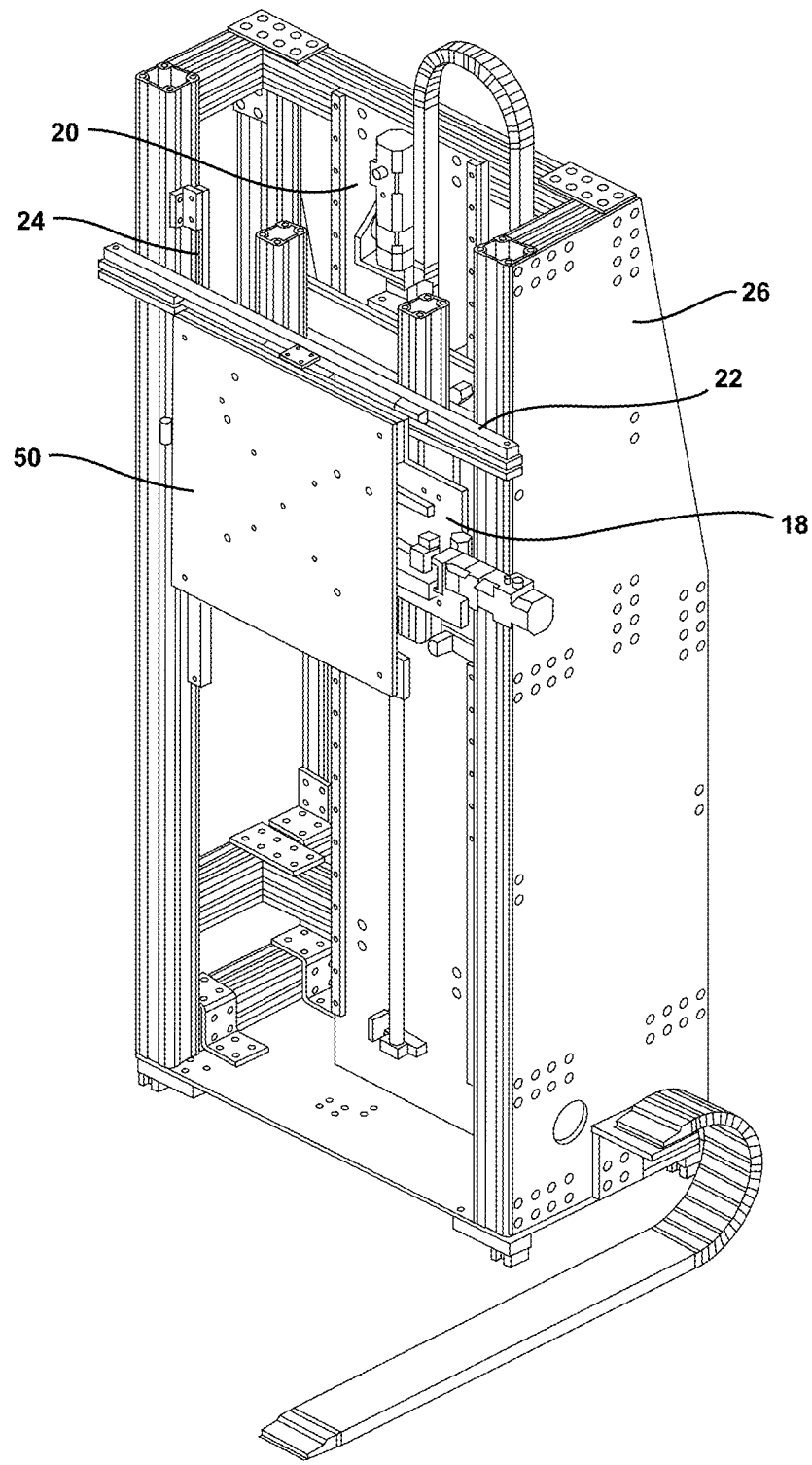
FIG. 2 is an illustration of an example implementation of the detector motion system, in accordance with one or more techniques of this disclosure.

FIG. 2 is a schematic illustration of an example detector motion system, in accordance with one or more techniques of this disclosure. The example detector motion system of FIG. 2 comprises detector mounting frame 26 to which radiation detector 14 (FIG. 1) may be mounted. Radiation detector 14 is not shown in the example of FIG. 2. Specifically, in the example of FIG. 2, a radiation detector (not shown in FIG. 2), such as a FPD, may be mounted on a detector mount 50 coupled to detector mounting frame 26. An x-ray source (not shown in FIG. 2) is mounted to direct an x-ray beam horizontally while the detector is at a position perpendicular to a main axis of the x-ray beam. In the example of FIG. 2, detector mount 50 (and hence the detector) is carried on horizontal translation stage 18 (i.e., x translation stage). Horizontal translation stage 18 is carried on vertical translation stage 20 (i.e., a y translation stage) coupled to detector mounting frame 26.

In the example of FIG. 2, each stage (i.e., horizontal translation stage 18 and vertical translation stage 20) has a linear encoder (i.e., a linear position encoder) mounted along an axis of the translation stage to measure the displacement of the translation stage. In the example of FIG. 2, linear encoder 22 (i.e., an x stage encoder) measures a displacement of horizontal translation stage 18 and linear encoder 24 (i.e., a y stage encoder) measures a displacement of vertical translation stage 20. Typical types of linear encoders include optical or magnetic tape encoders. In some examples, the resolution of the linear encoders is much finer than the pixel size. For example, an optical encoder may have a resolution finer than 1 μm resolution for a FPD with 100 μm pixel size.

In practical use, an image is first acquired at one position, followed by a series of additional images acquired with displacement at fractions of a pixel. For example, one additional image may be acquired at ½ pixel step translation, or three additional images may be acquired with ¼ pixel step translation. This may be performed for both horizontal and vertical axes to gain uniform resolution across the field of view. In certain scenarios where features are aligned in a single direction, movements along one axis may be sufficient. Images are then assembled in an interlaced fashion to produce a larger image with the same field of view but finer resolution. In some examples, some other methods (e.g., deconvolution or other techniques) can be used to further improve the resolution.

In some examples, the detector's movement can also be increased to nearly the size of the detector in order to increase the field of view. For example, acquiring two images separated by the size of the detector, and numerically stitching the two images may lead to a larger image with twice the field of view at the same resolution. In some implementations, it may be advantageous to acquire the images with some degree of over overlap, such as 10-20% of the linear size of the images, in order to accommodate more precise numerical stitching and intensity matching. A registering algorithm, such as a cross-correlation or a statistical pattern recognition method can be used to match the common areas with sub-pixel accuracy. This method may be used in both motion axes to increase the field of view in two dimensions. The linear encoders may be used to ensure the movement error is much smaller than the pixel size. In some implementations, more than two images in either or both direction can be stitched to increase the effective field of view.

In some examples, both sub-pixel sampling and stitching methods can be combined to both increase the field of view and increase the resolution. The trade-off of combining sub-pixel sampling and stitching methods may be more images required, which may increase exposure time and radiation dose. Either or both sub-pixel sampling and stitching methods can be combined with CT techniques to achieve greater field of view and resolution in 3D images. In some examples where a simple volumetric CT is used, projection images at each rotation angle are reconstructed from one or both techniques. However, this may require frequent movement of the translation stage. In some examples, a full CT series may be acquired through all projection (e.g., rotation) angles at one detector position, followed by full CT series at additional detector positions. Images at each projection angle and different detector positions may then be reconstructed and used in the CT reconstruction.

In addition to conventional volumetric CT, either or both sub-pixel sampling and stitching methods can also be combined with a spiral CT technique. As with the case of volumetric CT, either or both techniques can be first used to assemble a projection for each angle, then acquire the complete CT series. However, some implementations may acquire a full CT series through all projection angles at one detector position, followed by one or more CT series at one or more additional detector positions. Images from each projection angle and different detector positions may then be reconstructed and used in the CT reconstruction. Because the spiral motion can be used to cover a greater field of view along its axis, and spiral pitch may be adjusted to provide sub-pixel sampling, the sub-pixel sampling and stitching may only need to be applied along an axis perpendicular to the spiral axis. In effect, spiral techniques may be used to increase the field of view and resolution in a direction of the spiral axis while the sub-pixel sampling and stitching techniques may be used for the other axis.

Thus, the example detector motion system of FIG. 2 may form part of an x-ray imaging system comprising an x-ray generator (e.g., x-ray source 12 of FIG. 1) configured to emit an x-ray beam. Furthermore, the x-ray imaging system may comprise a two-dimensional pixelated area radiation detector having a plane arranged perpendicular to an emission direction of the x-ray beam. The radiation detector may be mounted to detector mount 50. A first translation stage (e.g., horizontal translation stage 18) and a second translation stage (e.g., vertical translation stage 20) carry the radiation detector. The first and second translation stages are configured to move the radiation detector along translation axes parallel to orientation directions of detector pixels of the radiation detector (e.g., horizontally and vertically).

Furthermore, the x-ray imaging system may comprise a first linear position encoder (e.g., linear encoder 22). The first linear position encoder has a resolution finer than one-quarter of a pixel size of the radiation detector. The first linear position encoder is configured to provide a direct measurement of displacement of the first translation stage. The x-ray imaging system may also comprise a second linear position encoder (e.g., linear encoder 24). The second linear position encoder may have a resolution finer than one-quarter the pixel size of the radiation detector. The second linear position encoder may be configured to provide a direct measurement of displacement of the second translation stage.

The x-ray imaging system may also comprise image acquisition system (e.g., image acquisition system 28). In some examples, the image acquisition system is configured to acquire a series of radiographs at different detector position along one or both axes separated by a distance finer than the pixel size of the radiation detector. In other examples, image acquisition system 28 is configured to acquire a series of radiographs at different detector positions (e.g., positions of radiation detector 14) along one or both translation axes separated by a distance less than a linear size of the radiation detector along the respective translation axis.

Furthermore, in some examples, the image acquisition system assembles the radiographs in an interlaced fashion to form a composite radiograph with finer resolution than the acquired radiographs. In other examples, the image acquisition system assembles the radiographs into a larger composite radiograph. In some such examples where the image acquisition system assembles the radiographs into a larger radiograph, the image acquisition system may use a cross-correlation algorithm to match edges of the radiographs prior to (or as part of) assembling the radiographs into the larger radiograph. Furthermore, in some examples where the image acquisition system assembles the radiographs into a larger radiograph, the image acquisition system may use an interpolation algorithm (or other appropriate type of algorithm) to blend intensities of the radiographs prior to (or as part of) assembling the radiographs into the larger radiograph.

Figure 3:
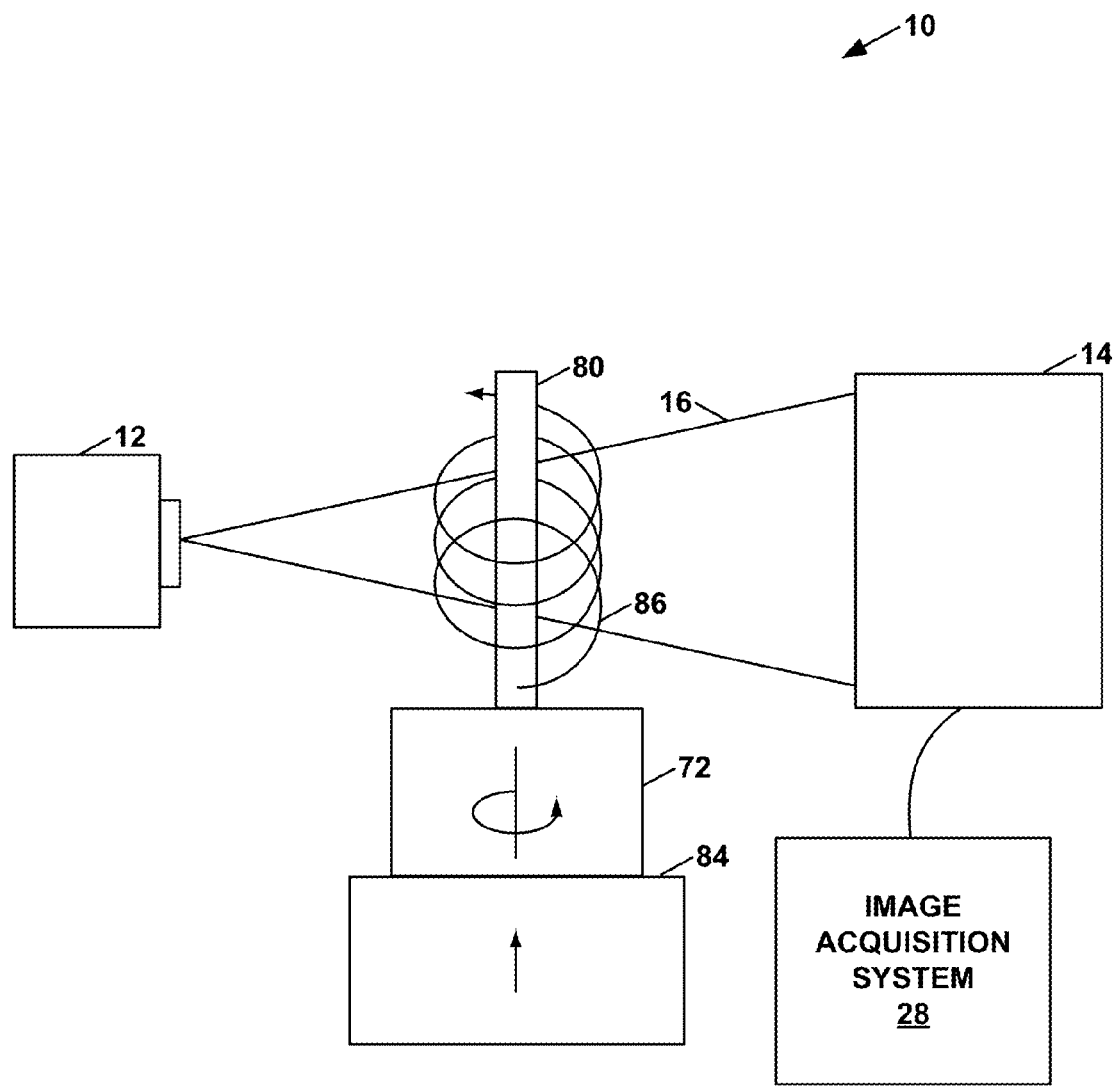
FIG. 3 is a schematic drawing of an. example instrumental setup in which an industrial computed tomography (CT) system includes a rotary stage, in accordance with one or more techniques of this disclosure.

FIG. 3 is a schematic drawing of an example instrumental setup in which an industrial CT system 10 includes a rotation stage 72, in accordance with one or more techniques of this disclosure. In the example of FIG. 3, industrial CT system 10 includes x-ray generator 12 configured to emit x-ray beam 16. Furthermore, industrial CT system 10 includes two-dimensional pixelated area radiation detector 14 having a plane arranged perpendicular to an emission direction of x-ray beam 16. Although not illustrated in the example of FIG. 3, a first translation stage and a second translation stage (e.g., x translation stage 18 and y translation stage 20) carry radiation detector 14. The first and second translation stages may be configured to move the radiation detector along translation axes parallel to orientation directions of detector pixels of the radiation detector. In the example of FIG. 3, rotation stage 72 has a rotation axis 80 perpendicular to the emission direction of x-ray beam 16. Rotation stage 72 is disposed between x-ray generator 74 and radiation detector 14. Rotation stage 72 is configured to carry and rotate a sample. Thus, industrial CT system 10 may comprise a rotation stage with its rotation axis perpendicular to the beam axis to carry and rotate a sample between x-ray generator 12 and radiation detector 14.

In accordance with one or more techniques of this disclosure, industrial CT system 10 may comprise a first linear position encoder (not shown in the example of FIG. 3). The first linear position encoder may have a resolution finer than one-quarter of a pixel size of radiation detector 14. The first linear position encoder may be configured to provide a direct measurement of displacement of the first translation stage. In addition, industrial CT system 10 may comprise a second linear position encoder (not shown in the example of FIG. 3). The second linear position encoder may have a resolution finer than one-quarter the pixel size of the radiation detector. The second linear position encoder may be configured to provide a direct measurement of displacement of the second translation stage.

Furthermore, in the example of FIG. 3, image acquisition system 28 may perform a computer reconstruction algorithm to process radiographs and assemble the radiographs into a 3D image representing a sample. For instance, image acquisition system 28 may be configured to acquire, while radiation detector 14 is at a first position, a first series of radiographs at a plurality of rotation angles. Furthermore, image acquisition system 28 may acquire, while radiation detector 14 is at a second position, a second series of radiographs at the plurality of rotation angles, the second position being separated from the first position along either or both the translation axes by a distance less than the pixel size of radiation detector 14. Image acquisition system 28 may generate, based on radiographs in the first series of radiographs and corresponding radiographs in the second series of radiographs, a series of higher-resolution composite radiographs. Furthermore, image acquisition system 28 may assemble the higher-resolution radiographs into a 3D radiograph of the sample.

In other examples, image acquisition system 28 is configured to acquire, while radiation detector 14 is at a first position, a first series of radiographs at a plurality of rotation angles. Furthermore, image acquisition system 28 may acquire, while radiation detector 14 is at a second position, a second series of radiographs at the same plurality of rotation angles. In such examples, the first position may be separated from the second position along one or both the translation axes by a distance less than a linear size (e.g., a height or width) of radiation detector 14 along the respective translation axis. Image acquisition system 28 may generate, based on radiographs in the first series of radiographs and corresponding radiographs in the second series of radiographs, a series (e.g., a plurality) of radiographs with larger fields of view. Image acquisition system 28 may assemble the generated series of radiographs into a 3-dimensional radiograph of the sample.

Thus, image acquisition system 28 may perform a computer-controlled image acquisition procedure in which a series of radiographs are acquired at different rotation angles. The series of radiographs are repeated at the same angular positions but at a different detector position along one or both axes separated by a distance finer than the detector pixel size. Subsequently, image acquisition system 28 may use a computer program to assemble the images at the same angle but different detector positions in an interlaced fashion to form a finer resolution image at this angle. Image acquisition system 28 may perform a computer reconstruction algorithm to assemble the finer-resolution radiographs into a 3D image representing the sample.

Furthermore, in some such examples, image acquisition system 28 may perform a computer-controlled image acquisition procedure in which large processed radiographs are acquired at different rotation angles. Furthermore, image acquisition system 28 may perform a computer construction algorithm to process the radiographs and assemble the radiographs into a 3D image representing the sample. Furthermore, in some such examples, image acquisition system 28 may perform a computer-controlled image acquisition procedure in which a series of radiographs are acquired at different rotation angles and repeated at the same angular positions but at different detector position along one or both axes separated by a distance between 50% and 100% of the detector linear size along the respective axis. Subsequently, image acquisition system 28 may use a computer program to assemble the images at the same angle but different detector positions to form a series of larger images at this angle. Image acquisition system 28 may perform a computer reconstruction algorithm to assemble the finer-resolution radiographs into a 3D image representing the sample.

In the example of FIG. 3, industrial CT system 10 comprises a linear stage 84. Linear stage 84 is configured to translate the sample linearly along an axis parallel to the rotation axis 80 of rotation stage 72. In other words, industrial CT system 10 comprises a linear stage with its axis parallel to a rotation stage that translates the sample. In some examples, a motion of rotation stage 72 and a motion of linear stage 84 are synchronized in a spiral pattern, as shown by arrow 86. In other words, a motion of rotation stage 72 and a motion linear stage 84 are synchronized so that the sample traces a spiral pattern in x-ray beam 16.

Furthermore, in the example of FIG. 3, image acquisition system 28 may acquire, while radiation detector 14 is at a first position, a first series of radiographs at a plurality of rotation angles and a plurality of linear stage positions. In addition, image acquisition system 28 may acquire, while radiation detector 14 is at a second position, a second series of radiographs at the plurality of rotation angles and the plurality of linear stage positions. The second position may be separated from the first position along either or both the translation axes by a distance less than the pixel size of radiation detector 14. Image acquisition system 28 may generate, based on radiographs in the first series of radiographs and corresponding radiographs in the second series of radiographs, a set of higher-resolution radiographs. The higher-resolution radiographs may have higher resolution than the radiographs in the first and second series of radiographs. Furthermore, image acquisition system 28 may assemble the higher-resolution radiographs into a 3-dimensional radiograph of the sample.

Thus, in some examples, image acquisition system 28 may perform a computer-controlled image acquisition procedure in which a series of radiographs are acquired at different rotation angles and sample linear stage positions. The series of radiographs is repeated at the same rotation and linear stage position settings but at a different detector position along one or both axes of movement of the translation stages separated by a distance finer than the detector pixel size. Image acquisition system 28 may subsequently use a computer program to assemble the images at the same angular and linear positions but different detector positions in an interlaced fashion to form a finer resolution image at this angle. Image acquisition system 28 may also perform a computer reconstruction algorithm to assemble the finer-resolution radiographs into a 3D image representing the sample.

In a similar example, image acquisition system 28 may perform a computer-controlled image acquisition procedure in which a series of radiographs are acquired at different rotation angles and source and detector common axis positions. The series of radiographs are repeated at the same rotation and linear stage position settings but at a different detector position along one or both axes separated by a distance finer than the detector pixel size. Subsequently, image acquisition system 28 may use a computer program to assemble the images at the same angular and linear positions but different detector positions in an interlaced fashion to form a finer resolution image at this angle. Finally, in this example, image acquisition system 28 may perform a computer reconstruction algorithm to assemble the finer-resolution radiographs into a 3D image representing the sample.

As indicated above, an image acquisition system may, in some examples, assemble radiographs into a larger radiograph. Such examples may be applicable to the example of FIG. 3. Thus, in some examples, a x-ray imaging system e.g., industrial CT system 10) may comprise rotation stage 72 having rotation axis 80 perpendicular to the emission direction of x-ray beam 16. As before, rotation stage 72 is disposed between x-ray generator 74 and radiation detector 14 and is configured to carry and rotate a sample. In some such examples, image acquisition system 28 is configured to acquire radiographs at different detector positions for different rotation angles. Image acquisition system 28 may be configured to process the radiographs to assemble the radiographs into a 3-dimensional radiograph of the sample.

Thus, in some examples, image acquisition system 28 may perform an image acquisition procedure comprising (e.g., consisting of) acquiring a series of images at different detector position along one or both axes separated by a distance between 50% and 100% of the detector linear size along the respective axis. In such examples, image acquisition system 28 may use a computer program to assemble the images into a larger image.

In other examples, image acquisition system 28 acquires, while radiation detector 14 is at a first position, a first series of radiographs at a plurality of rotation angles and a plurality of linear stage positions. In addition, image acquisition system 28 may acquire, while radiation detector 14 is at a second position, a second series of radiographs at the plurality of rotation angles and the plurality of linear stage positions. As in other examples, the first position is separated from the second position along one or both the translation axes by a distance less than a linear size of the radiation detector along the respective translation axis. Furthermore, image acquisition system 28 may generate, based on radiographs in the first series of radiographs and corresponding radiographs in the second series of radiographs, a series of radiographs with larger fields of view. Image acquisition system 28 may then assemble the generated series of radiographs into a 3-dimensional radiograph of the sample. This 3-dimensional radiograph may have a larger field of view than a corresponding 3-dimensional radiograph based only on a single series of radiographs from a single position of radiation detector 14.

In some such examples, image acquisition system 28 may perform a computer-controlled image acquisition procedure in which a series of radiographs acquired at different rotation angles and sample linear stage positions and repeated at the same rotation and linear stage position settings but at different detector position along one or both axes separated by a distance between 50% and 100% of the detector linear size along the respective axis. In some instances, image acquisition system 28 may subsequently use a computer program to assemble the images at the same angular and linear positions but different detector positions to form a series of larger images at this angle. In some instances, image acquisition system 28 may subsequently use a computer program to assemble the images at the same angular and linear positions but different radiation detector positions to form a series of larger images at this angular and position setting. Finally, in some such examples, image acquisition system 28 may use a computer reconstruction algorithm to assemble the finer-resolution radiographs into a 3D image representing the sample.

In other examples, industrial CT system 10 does not comprise rotational stage 72. Rather, industrial CT system 10 may comprise a non-rotational stage mounted on linear stage 84. Linear stage 84 may be configured to translate the sample linearly along an axis (e.g., axis 80) perpendicular to x-ray beam 16. In such examples, industrial CT system 10 may generate similar 3-dimensional radiographs by rotating x-ray generator 74 and radiation detector 14 around the sample. In some such examples, image acquisition system 78 may acquire, while radiation detector 14 is at a first position, a first series of radiographs at a plurality of rotation angles and a plurality of x-ray generator 74 and radiation detector 14 positions (i.e., positions of x-ray generator 74 and radiation detector 14). In addition, image acquisition system 28 may acquire, while radiation detector 14 is at a second position, a second series of radiographs at the plurality of rotation angles and the plurality of x-ray generator 74 and radiation detector 14 positions. The second position may be separated from the first position along either or both the translation axes by a distance less than the pixel size of the radiation detector. Image acquisition system 28 may generate, based on radiographs in the first series of radiographs and corresponding radiographs in the second series of radiographs, a set of higher-resolution radiographs. The higher-resolution radiographs have higher resolution than the radiographs in the first and second series of radiographs. Image acquisition system 28 may assemble the higher-resolution radiographs into a 3-dimensional radiograph of the sample.

In still other examples where x-ray generator 74 and radiation detector 14 may rotate around the sample, image acquisition system 28 may acquire, while radiation detector 14 is at a first position, a first series of radiographs at a plurality of rotation angles and a plurality of x-ray generator 74 and radiation detector 14 positions (i.e., positions of x-ray generator 74 and radiation detector 14). Image acquisition system 28 may also acquire, while radiation detector 74 is at a second position, a second series of radiographs at the plurality of rotation angles and the plurality of x-ray generator 74 and radiation detector 14 positions, wherein the first position is separated from the second position along one or both the translation axes by a distance less than a linear size of the radiation detector along the respective translation axis. Image acquisition system 28 may generate, based on radiographs in the first series of radiographs and corresponding radiographs in the second series of radiographs, a series of radiographs with larger fields of view. In addition, image acquisition system 28 may assemble the generated series of radiographs into a 3-dimensional radiograph of the sample.

Figure 4:
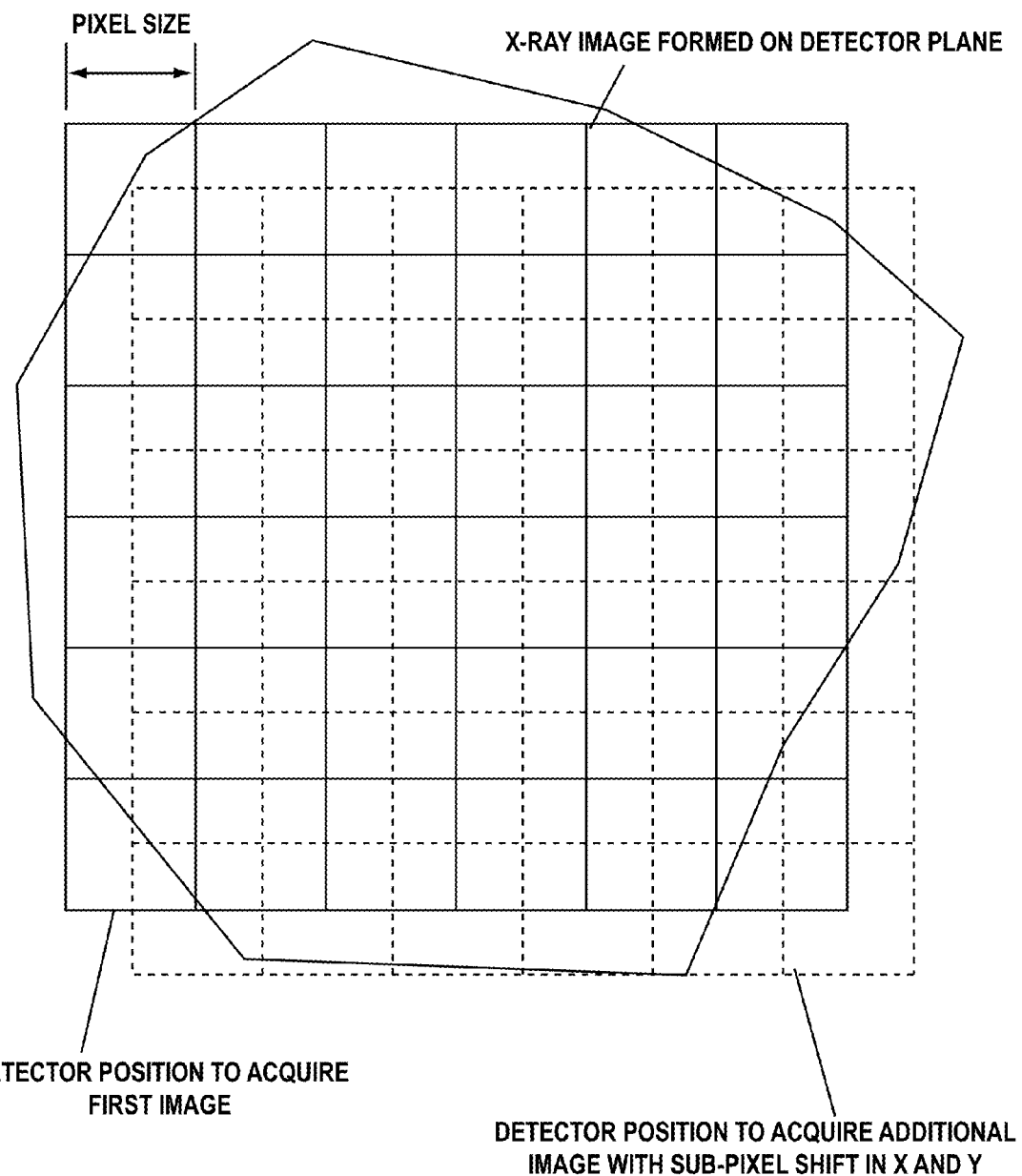
FIG. 4 is a conceptual diagram illustrating an example super-resolution image acquisition process, in accordance with one or more techniques of this disclosure.

FIG. 4 is a conceptual diagram illustrating an example super-resolution image acquisition process, in accordance with one or more techniques of this disclosure. In the example of FIG. 4, a grid of solid lines indicates positions of pixels of a radiation detector while the radiation detector is at a first position. A grid of dashed lines indicates positions of the pixels of the radiation detector while the radiation detector is at a second position. The smaller squares formed by the overlap of the grids may indicate pixels in a higher-resolution radiograph based on radiographs acquired while the radiation detector was at the first and second positions.

Figure 5A:
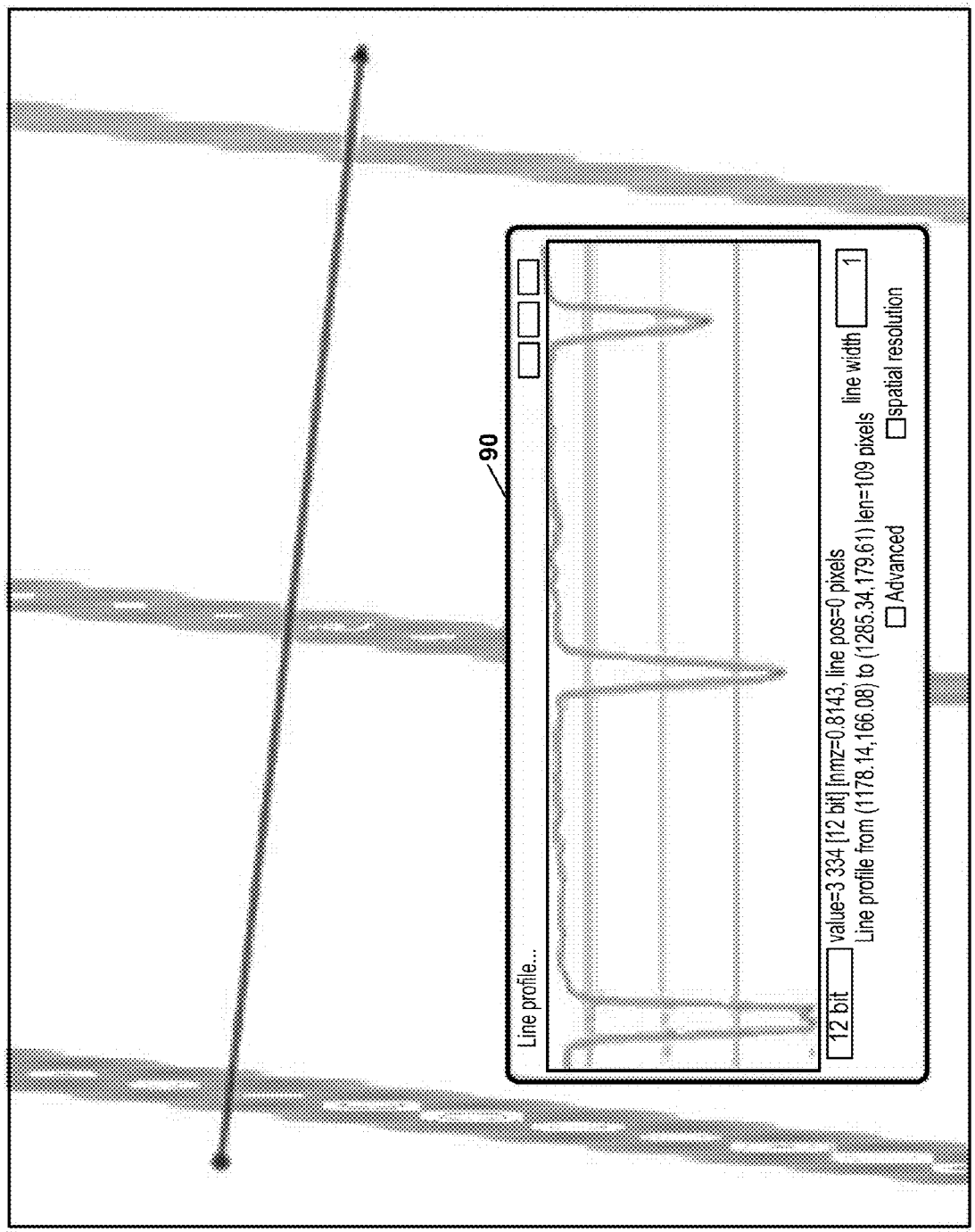
FIG. 5A illustrates an example conventional x-ray radiograph.
Figure 5B:
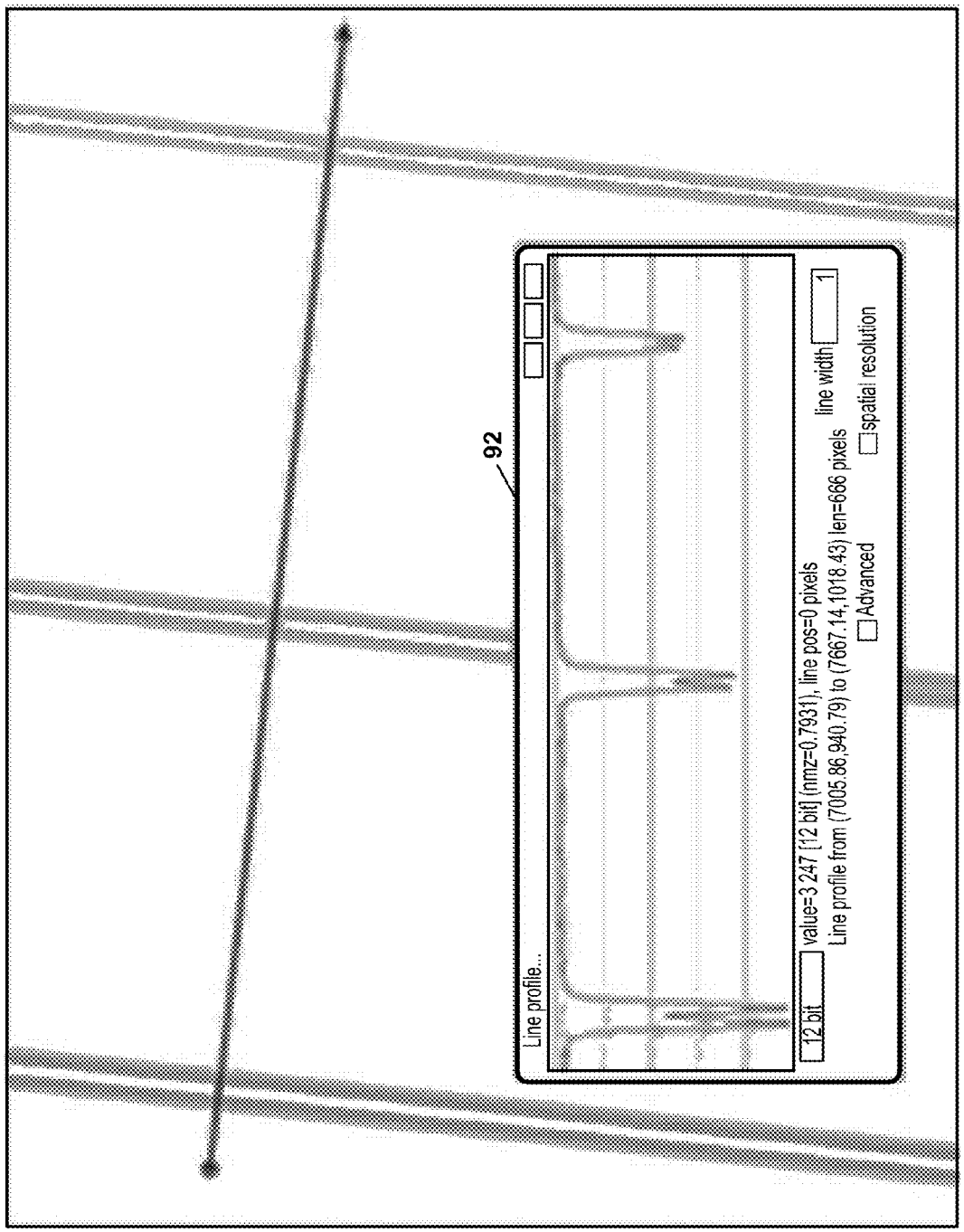
FIG. 5B illustrates an example super-resolved x-ray radiograph captured in accordance with one or more techniques of this disclosure.

FIG. 5A illustrates an example conventional x-ray radiograph. FIG. 5B illustrates an example super-resolved x-ray radiograph captured in accordance with one or more techniques of this disclosure. More specifically, FIGS. 5A and 5B are x-ray images of a line-pair test acquired with a flat panel detector. FIG. 5B is an x-ray image of a line-pair test acquired with the same flat panel detector at four sub-pixel positions separated by one-fourth of a pixel size and assembled by interlacing the four images. Comparing these two features, the three pairs of parallel lines are resolved more clearly with better rate of sampling in FIG. 5B than FIG. 5A. In this way, pixels from different radiographs may be interlaced.

In the examples of FIGS. 5A and 5B, inset windows 90, 92 show relative intensities as functions. In the example of FIG. 5A, the function does not show significant differentiation between individual lines in the pairs of parallel lines. However, in the example of FIG. 5B, the function shown in the inset window indicates more significant differentiation between individual lines in the pairs of parallel lines, especially for the rightmost pair of parallel lines.

Figure 6:
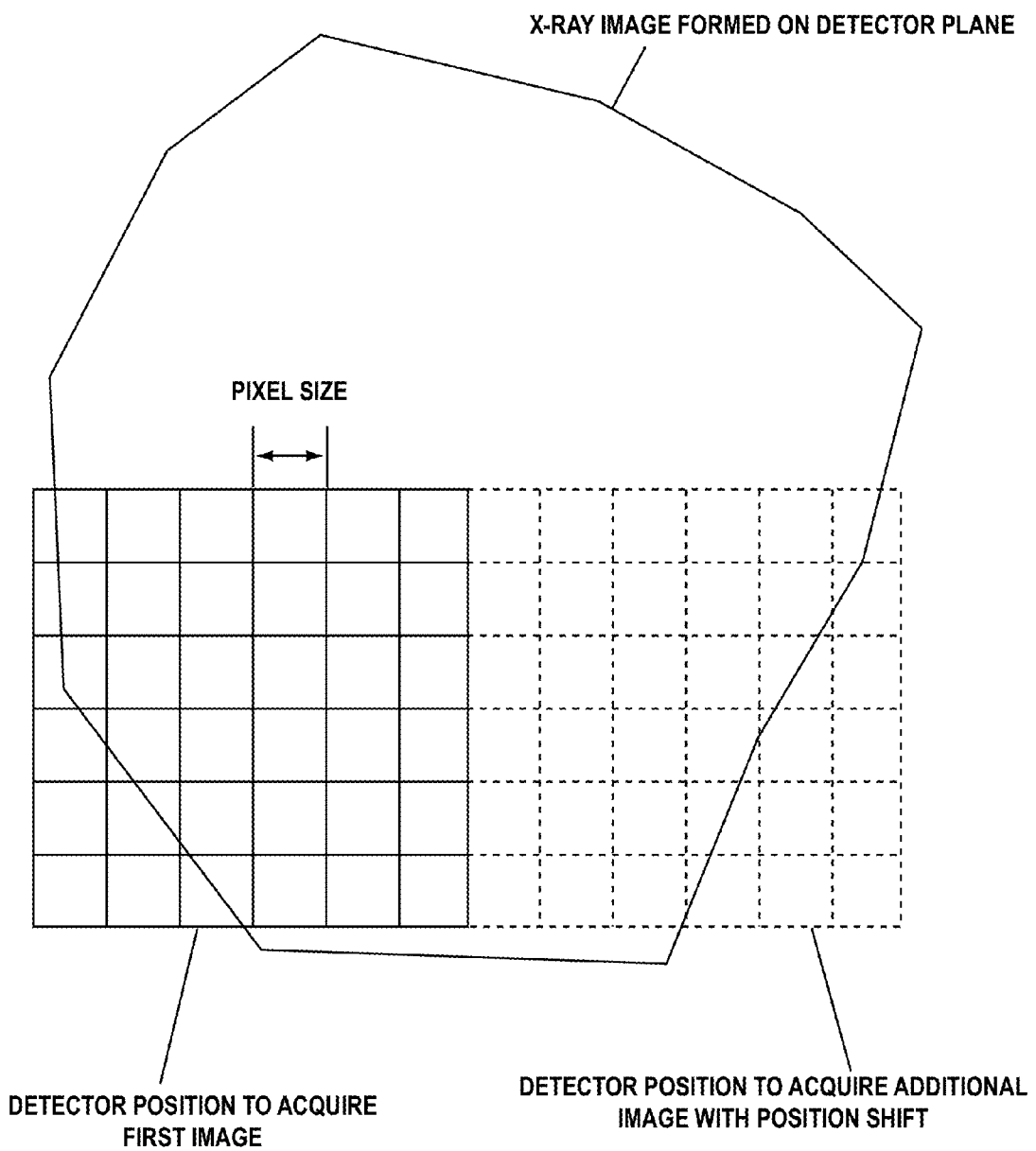
FIG. 6 is a conceptual diagram illustrating an example mosaic image acquisition and assembly process, in accordance with one or more techniques of this disclosure.

FIG. 6 is a conceptual diagram illustrating an example mosaic image acquisition and assembly process, in accordance with one or more techniques of this disclosure. In the example of FIG. 6, a grid of solid lines indicates positions of pixels of a radiation detector while the radiation detector is at a first position. A grid of dashed lines indicates positions of the pixels of the radiation detector while the radiation detector is at a second position. The combination of the solid line and dashed line grids may indicate pixels in a larger radiograph "stitched" together from radiographs acquired while the radiation detector was at the first and second positions. Although FIG. 6 shows two images separated by exactly the detector width, the two images may, in some implementations, have an overlap as described elsewhere in this disclosure.

In some examples, generating a set of radiographs with larger fields of view comprises, for each respective rotation angle from the plurality of rotation angles, assembling, based on a first applicable radiograph and a second applicable radiograph, a radiograph for the respective rotation angle. The first applicable radiograph is in the first series of radiographs and is associated with the respective rotation angle. The second applicable radiograph is in the second series of radiographs and is associated with the respective rotation angle, wherein the assembled radiograph has a larger field of view than the first or second applicable radiographs. In some implementations, more than two radiographs in either or both direction along the detector rows and columns can be combined.

Figure 7:
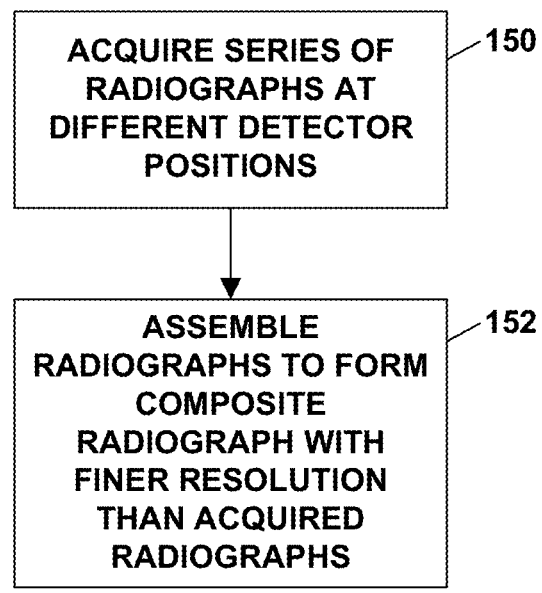
FIG. 7 is a flowchart illustrating an example operation of an industrial CT system, in accordance with one or more techniques of this disclosure.

FIG. 7 is a flowchart illustrating an example operation of an industrial CT system, in accordance with one or more techniques of this disclosure. The example operation of FIG. 7 is explained with reference to the example of FIG. 1. However, the example operation of FIG. 7 is not so limited.

In the example of FIG. 7, image acquisition system 28 acquires a series of radiographs at different detector positions along a first translation axis or a second translation axis parallel to orientation directions of detector pixels of radiation detector 14 (150). The different detector positions may be separated by a distance finer than a pixel size of radiation detector 14. Radiation detector 14 may have a plane arranged perpendicular to an emission direction of x-ray beam 16 emitted by x-ray generator 12. A first translation stage (e.g., x translation stage 18) and a second translation stage (e.g., y translation stage 20) carry radiation detector 14. The first and second translation stages may be configured to move radiation detector 14 along the first and second translation axes. Furthermore, in the example of FIG. 7, image acquisition system 28 may assemble two or more of the radiographs to form a composite radiograph with finer resolution than the acquired radiographs (152).

Figure 8:
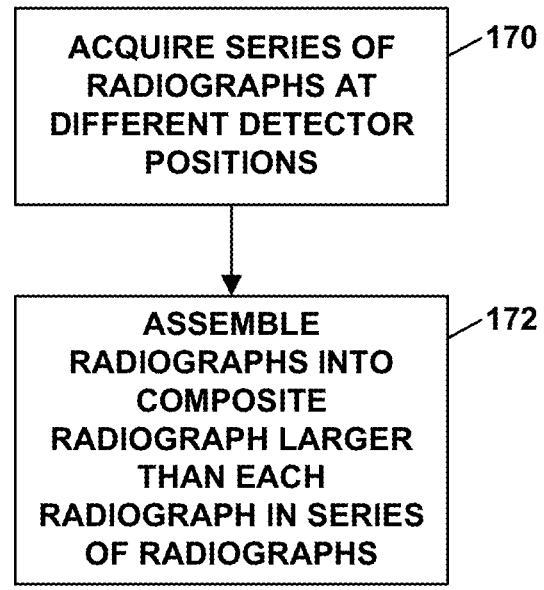
FIG. 8 is a flowchart illustrating an example operation of an industrial CT system, in accordance with one or more techniques of this disclosure.

FIG. 8 is a flowchart illustrating an example operation of an industrial CT system, in accordance with one or more techniques of this disclosure. The example operation of FIG. 8 is explained with reference to the example of FIG. 1. However, the example operation of FIG. 8 is not so limited.

In the example of FIG. 8, image acquisition system 28 acquires a series of radiographs at different detector positions along a first translation axis or a second translation axis parallel to orientation directions of detector pixels of radiation detector 14 (170). The different detector positions may be separated by a distance less than a linear size of radiation detector 14 along the first translation axis or the second translation axis, respectively. Radiation detector 14 has a plane arranged perpendicular to an emission direction of x-ray beam 16 emitted by x-ray generator 12. A first translation stage (e.g., x translation stage 18) and a second translation stage (e.g., y translation stage 20) may carry radiation detector 14. The first and second translation stages may be configured to move radiation detector 14 along the first and second translation axes. Furthermore, in the example of FIG. 8, image acquisition system 28 may assemble two or more of the radiographs into a composite radiograph larger than each radiograph in the series of radiographs (172).

The following paragraphs provide additional example techniques of this disclosure.

EXAMPLE 1

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a first linear position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire a series of radiographs at different detector position along one or both axes separated by a distance finer than the pixel size of the radiation detector, and assemble the radiographs in an interlaced fashion to form a radiograph with finer resolution than the acquired radiographs.

EXAMPLE 2

The x-ray imaging system of example 1, wherein the x-ray generator generates x-rays with an energy range of 20 keV to 600 keV.

EXAMPLE 3

The x-ray imaging system of examples 1 or 2, wherein: the radiation detector comprises a flat-panel x-ray detector, and the pixel size of the radiation detector is in a range of 25 micrometers to 250 micrometers.

EXAMPLE 4

The x-ray imaging system of any of example 1-3, wherein: the radiation detector comprises a lens-coupled detector, and the pixel size of the radiation detector is in a range of 0.1 micrometers to 10 micrometers.

EXAMPLE 5

The x-ray imaging system of any of examples 1-4, wherein the x-ray imaging system further comprises a rotation stage having a rotation axis perpendicular to the emission direction of the x-ray beam, wherein the rotation stage is disposed between the x-ray generator and the radiation detector, wherein the rotation stage is configured to carry and rotate a sample; wherein the computing system is configured to: acquire radiographs at different detector positions for different rotation angles; and process the radiographs to assemble the radiographs into a 3-dimensional radiograph of the sample.

EXAMPLE 6

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a first position encoder, wherein the first linear position encoder has a resolution finer than one-quarter of a pixel size of the radiation detector, wherein the first linear position encoder is configured to provide a direct measurement of displacement of the first translation stage; a second linear, position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles; acquire, white the radiation detector is at a second position, a second series of radiographs at the plurality of rotation angles, the second position being separated from the first position along either or both the translation axes by a distance less than the pixel size of the radiation detector; generate, based on radiographs in the first series of radiographs and corresponding radiographs in the second series of radiographs, a series of higher-resolution radiographs; and assemble the higher-resolution radiographs into a 3D radiograph of the sample.

EXAMPLE 7

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a linear stage configured to translate the sample linearly along an axis parallel to the rotation axis of the rotation stage; a first linear position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles and a plurality of linear stage positions; acquire, while the radiation detector is at a second position, a second series of radiographs at the plurality of rotation angles and the plurality of linear stage positions, the second position being separated from the first position along either or both the translation axes by a distance less than the pixel size of the radiation detector; generate, based on radiographs in the first series of radiographs and corresponding radiographs in the second series of radiographs, a set of higher-resolution radiographs, wherein the higher-resolution radiographs have higher resolution than the radiographs in the first and second series of radiographs; and assemble the higher-resolution radiographs into a 3-dimensional radiograph of the sample.

EXAMPLE 8

The x-ray imaging system of example 7, wherein a motion of the rotation stage and a motion of the linear stage are synchronized in a spiral pattern.

EXAMPLE 9

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a linear stage configured to translate the sample linearly along an axis parallel to the rotation axis of the rotation stage; a first position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles and a plurality of x-ray source and radiation detector positions; acquire, while the radiation detector is at a second position, a second series of radiographs at the plurality of rotation angles and the plurality of x-ray source and radiation detector positions, the second position being separated from the first position along either or both the translation axes by a distance less than the pixel size of the radiation detector; generate, based on radiographs in the first series of radiographs and corresponding radiographs in the second series of radiographs, a set of higher-resolution radiographs, wherein the higher-resolution radiographs have higher resolution than the radiographs in the first and second series of radiographs; and assemble the higher-resolution radiographs into a 3-dimensional radiograph of the sample.

EXAMPLE 10

The x-ray imaging system of example 9, wherein the motion of the rotation stage and linear translations stage are synchronized so that the sample traces a spiral pattern in the x-ray beam.

EXAMPLE 11

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a first linear position encoder, wherein the first linear position encoder has a resolution finer than one-quarter of a pixel size of the radiation detector, wherein the first linear position encoder is configured to provide a direct measurement of displacement of the first translation stage; a second linear detector, wherein the second linear detector has a resolution finer than one-quarter the pixel size of the radiation detector, wherein the second linear detector is configured to provide a direct measurement of displacement of the second translation stage; and an image acquisition system configured to: acquire a series of radiographs at different detector position along one or both translation axes separated by a distance less than a linear size of the radiation detector along the respective translation axis; and assemble the radiographs into a larger radiograph.

EXAMPLE 12

The x-ray imaging system of example 11, wherein the x-ray generator generates x-rays with an energy range of 20 keV to 600 keV.

EXAMPLE 13

The x-ray imaging system of examples 11 or 12, wherein: the radiation detector comprises a flat-panel x-ray detector, and the pixel size of the radiation detector is in the range of 25 micrometers to 250 micrometers.

EXAMPLE 14

The x-ray imaging system of any of examples 11-13, wherein: the radiation detector comprises a lens-coupled detector, and the pixel size of the radiation detector is in the range of 0.1 micrometers to 10 micrometers.

EXAMPLE 15

The x-ray imaging system of any of examples 11-14, wherein the image acquisition system is further configured to use a cross-correlation algorithm to match edges of the radiographs prior to assembling the radiographs into the larger radiograph.

EXAMPLE 16

The x-ray imaging system of any of examples 11-15, wherein the image acquisition system is further configured to use an interpolation algorithm to blend an intensity of the radiographs prior to assembling the radiographs into the larger radiograph.

EXAMPLE 17

The x-ray imaging system of any of examples 11-16, further comprising: wherein the x-ray imaging system further comprises a rotation stage having a rotation axis perpendicular to the emission direction of the x-ray beam, wherein the rotation stage is disposed between the x-ray generator and the radiation detector, wherein the rotation stage is configured to carry and rotate a sample; wherein the image acquisition system is configured to: acquire radiographs at different detector positions for different rotation angles; and process the radiographs to assemble the radiographs into a 3-dimensional radiograph of the sample.

EXAMPLE 18

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a first linear position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles; acquire, while the radiation detector is at a second position, a second series of radiographs at the plurality of rotation angles, wherein the first position is separated from the second position along one or both the translation axes by a distance less than a linear size of the radiation detector along the respective translation axis; generate, based on radiographs in the first series of radiographs and corresponding radiographs in the second series of radiographs, a series of radiographs with larger fields of view; and assemble the generated series of radiographs into a 3-dimensional radiograph of the sample.

EXAMPLE 19

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a linear stage configured to translate the sample linearly along an axis parallel to the rotation axis of the rotation stage; a first linear, position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles and a plurality of linear stage positions; acquire, while the radiation detector is at a second position, a second series of radiographs at the plurality of rotation angles and the plurality of linear stage positions, wherein the first position is separated from the second position along one or both the translation axes by a distance less than a linear size of the radiation detector along the respective translation axis; generate, based on radiographs in the first series of radiographs and corresponding radiographs in the second series of radiographs, a series of radiographs with larger fields of view; and assemble the generated series of radiographs into a 3-dimensional radiograph of the sample.

EXAMPLE 20

The x-ray imaging system of example 19, wherein a motion of the rotation stage and a motion of the linear stage are synchronized in a spiral pattern of motion.

EXAMPLE 21

An x-ray imaging system comprising: an x-ray generator configured to emit an x-ray beam; a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; a rotation stage having a rotation axis perpendicular to the emission direction of the x-ray beam, wherein the rotation stage is disposed between the x-ray generator and the radiation detector, wherein the rotation stage is configured to carry and rotate a sample; a linear stage configured to translate the sample linearly along an axis parallel to the rotation axis of the rotation stage; a first linear position encoder, wherein the first linear position encoder has a resolution finer than one-quarter of a pixel size of the radiation detector, wherein the first linear position encoder is configured to provide a direct measurement of displacement of the first translation stage; a second linear position encoder, wherein the second linear position encoder has a resolution finer than one-quarter the pixel size of the radiation detector, wherein the second linear position encoder is configured to provide a direct measurement of displacement of the second translation stage; an image acquisition system configured to: acquire, while the radiation detector is at a first position, a first series of radiographs at a plurality of rotation angles and a plurality of x-ray source and radiation detector positions; acquire, while the radiation detector is at a second position, a second series of radiographs at the plurality of rotation angles and the plurality of x-ray source and radiation detector positions, wherein the first position is separated from the second position along one or both the translation axes by a distance less than a linear size of the radiation detector along the respective translation axis; generate, based on radiographs in the first series of radiographs and corresponding radiographs in the second series of radiographs, a series of radiographs with larger fields of view; and assemble the generated series of radiographs into a 3-dimensional radiograph of the sample.

EXAMPLE 22

The x-ray imaging system of example 21, wherein a motion of the rotation stage and a motion of the linear stage are synchronized so that the sample traces a spiral pattern in the x-ray beam.

EXAMPLE 23

An x-ray imaging system configured according to any of examples 1-22.

EXAMPLE 24

An x-ray imaging system according to any of technique disclosed herein.

EXAMPLE 25

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; two independent linear encoders with resolution finer than quarter of the detector pixel size and arranged in parallel to the two stages, and are driven by the respect stages to provide direct measurement of displacement; and a computer-controlled image acquisition procedure consisting of acquiring a series of images at different detector position along one or both axes separated by a distance finer than the detector pixel size, and using a computer program to assemble the images in a interlaced fashion to form a finer resolution image.

EXAMPLE 26

The apparatus of example 25, where the x-ray generator provides x-rays with energy range of 20 keV to 600 keV.

EXAMPLE 27

The apparatus of examples 25 or 26, comprising a flat-panel x-ray detector with pixel size in the range of 25 micrometers to 250 micrometers.

EXAMPLE 28

The apparatus of any of examples 25-27, comprising a lens-coupled detector with pixel size in the range of 0.1 micrometers to 10 micrometers.

EXAMPLE 29

The apparatus of any of examples 25-28, comprising: a rotation stage with its rotation axis perpendicular to the beam axis to carry and rotate the sample between the source and detector; a computer-controlled image acquisition procedure in which radiographs acquired at different detector position for different rotation angles; a computer reconstruction algorithm to process the radiographs and assemble them into a 3D image representing the sample.

EXAMPLE 30

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; two independent linear encoders with resolution finer than quarter of the detector pixel size and arranged in parallel to the two stages, and are driven by the respect stages to provide direct measurement of displacement; a computer-controlled image acquisition procedure in which a series of radiographs acquired at different rotation angles; and repeated at the same angular positions but at different detector position along one or both axes separated by a distance finer than the detector pixel size; subsequently using a computer program to assemble the images at the same angle but different detector positions in a interlaced fashion to form a finer resolution image at this angle; and finally a computer reconstruction algorithm to assemble the finer-resolution radiographs into a 3D image representing the sample.

EXAMPLE 31

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; a linear stage with its axis parallel to the rotation stage that translates the sample; two independent linear encoders with resolution finer than quarter of the detector pixel size and arranged in parallel to the two stages, and are driven by the respect stages to provide direct measurement of displacement; a computer-controlled image acquisition procedure in which a series of radiographs acquired at different rotation angles and sample linear stage positions; and repeated at the same rotation and linear stage position settings but at different detector position along one or both axes separated by a distance finer than the detector pixel size; subsequently using a computer program to assemble the images at the same angular and linear positions but different detector positions in a interlaced fashion to form a finer resolution image at this angle; and finally a computer reconstruction algorithm to assemble the finer-resolution radiographs into a 3D image representing the sample.

EXAMPLE 32

The apparatus and imaging acquisition method of example 31, in which the motion of the rotation stage and linear translations stage are synchronized in a spiral pattern.

EXAMPLE 33

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; a linear stage with its axis parallel to one of the detector axis that translates the x-ray source and furthermore with its motion synchronized to the detector motion axis; two independent linear encoders with resolution finer than quarter of the detector pixel size and arranged in parallel to the two stages, and are driven by the respect stages to provide direct measurement of displacement; and a computer-controlled image acquisition procedure in which a series of radiographs acquired at different rotation angles and source and detector common axis positions; and repeated at the same rotation and linear stage position settings but at different detector position along one or both axes separated by a distance finer than the detector pixel size; subsequently using a computer program to assemble the images at the same angular and linear positions but different detector positions in a interlaced fashion to form a finer resolution image at this angle; and finally a computer reconstruction algorithm to assemble the finer-resolution radiographs into a 3D image representing the sample.

EXAMPLE 34

The apparatus and imaging acquisition method of example 33, in which the motion of the rotation stage and linear translations stage are synchronized so that the sample traces a spiral pattern in the x-ray beam.

EXAMPLE 35

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; two independent linear encoders with resolution finer than quarter of the detector pixel size and arranged in parallel to the two stages, and are driven by the respect stages to provide direct measurement of displacement; and an image acquisition procedure consisting of acquiring a series of images at different detector position along one or both axes separated by a distance between 50% and 100% of the detector linear size along the respective axis; and using a computer program to assemble the images into a larger image.

EXAMPLE 36

The apparatus of example 35, where the x-ray generator provides x-rays with energy range of 20 keV to 600 keV.

EXAMPLE 37

The apparatus of examples 35 or 36, comprising a flat-panel x-ray detector with pixel size in the range of 25 micrometers to 250 micrometers.

EXAMPLE 38

The apparatus of any of examples 35-37 comprising a lens-coupled detector with pixel size in the range of 0.1 micrometers to 10 micrometers.

EXAMPLE 39

The apparatus of any of examples 35-38, in which a cross-correlation algorithm is used to match edges of the acquired images prior to assembling the images.

EXAMPLE 40

The apparatus of any of examples 35-39, in which a linear-interpolation algorithm is used to match the intensity of the acquired images prior to assembling the images.

EXAMPLE 41

The apparatus of any of examples 35-40, comprising: a rotation stage with its rotation axis perpendicular to the beam axis to carry and rotate the sample between the source and detector; a computer-controlled image acquisition procedure in which large processed radiographs are acquired as different rotation angles; and a computer reconstruction algorithm to process the radiographs and assemble them into a 3D image representing the sample.

EXAMPLE 42

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; two independent linear encoders with resolution finer than quarter of the detector pixel size and arranged in parallel to the two stages, and are driven by the respect stages to provide direct measurement of displacement; and a computer-controlled image acquisition procedure in which a series of radiographs acquired at different rotation angles; and repeated at the same angular positions but at different detector position along one or both axes separated by a distance between 50% and 100% of the detector linear size along the respective axis; subsequently using a computer program to assemble the images at the same angle but different detector positions to form a series of larger images at this angle; and finally a computer reconstruction algorithm to assemble the finer-resolution radiographs into a 3D image representing the sample.

EXAMPLE 43

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; a linear stage with its axis parallel to the rotation stage that translates the sample; two independent linear encoders with resolution finer than quarter of the detector pixel size and arranged in parallel to the two stages, and are driven by the respect stages to provide direct measurement of displacement; and a computer-controlled image acquisition procedure in which a series of radiographs acquired at different rotation angles and sample linear stage positions; and repeated at the same rotation and linear stage position settings but at different detector position along one or both axes separated by a distance between 50% and 100% of the detector linear size along the respective axis; subsequently using a computer program to assemble the images at the same angular and linear positions but different detector positions to form a series of larger images at this angle; and finally a computer reconstruction algorithm to assemble the finer-resolution radiographs into a 3D image representing the sample.

EXAMPLE 44

The apparatus and imaging acquisition method of example 43, in which the motion of the rotation stage and linear translations stage are synchronized in a spiral pattern.

EXAMPLE 45

An x-ray imaging apparatus and image acquisition procedure comprising: an x-ray generator; a two-dimensional pixelated area radiation detector with its plane arranged perpendicular to the emission direction of x-ray beam (beam axis), and carried on two independent translation stages with each axis parallel to the orientation of the detector pixels; a rotation stage with its rotation axis perpendicular to the beam axis to carry and rotate the sample between the source and detector; a linear stage with its axis parallel to one of the detector axis that translates the x-ray source and furthermore with its motion synchronized to the detector motion axis; two independent linear encoders with resolution finer than quarter of the detector pixel size and arranged in parallel to the two stages, and are driven by the respect stages to provide direct measurement of displacement; and a computer-controlled image acquisition procedure in which a series of radiographs acquired at different rotation angles and source and detector common axis positions; and repeated at the same rotation and linear stage position settings but at different detector position along one or both axes separated 50% and 100% of the detector linear size along the respective axis; subsequently using a computer program to assemble the images at the same angular and linear positions but different detector positions to form a series of larger images at this angular and position setting; and finally a computer reconstruction algorithm to assemble the finer-resolution radiographs into a 3D image representing the sample.

EXAMPLE 46

The apparatus and imaging acquisition method of example 45, in which the motion of the rotation stage and linear translations stage are synchronized so that the sample traces a spiral pattern in the x-ray beam.

EXAMPLE 47

An x-ray imaging system configured according to any of examples 1-46.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

In one or more examples, particular functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readably; storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the "term processor," as used herein may refer to any of the foregoing structure or any other structure suitable for implementation of the techniques described herein. In addition, in some aspects, the functionality described herein may be provided within dedicated hardware and/or software modules. Also, particular portions of the techniques may be implemented in one or more circuits or logic elements.

Various examples have been described. These and other examples are within the scope of the following claims.

What is claimed is:

1. An x-ray imaging system comprising:
an x-ray generator configured to emit an x-ray beam;
a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector; and a rotation stage having a rotation axis perpendicular to the emission direction of the x-ray beam, wherein the rotation stage is disposed between the x-ray generator and the radiation detector, wherein the rotation stage is configured to carry and rotate a sample;

a linear stage configured to translate the sample linearly along an axis parallel to the rotation axis of the rotation stage, wherein a motion of the rotation stage and a motion of the linear stage are synchronized such that the x-ray beam traces a spiral pattern on the sample; and an image acquisition system configured to:
  acquire, while the radiation detector is at a first detector position, a first series of radiographs at a plurality of rotation angles of the rotation stage and a plurality of linear stage positions of the linear stage;
  after acquiring the first series of radiographs, acquire, while the radiation detector is at a second detector position, a second series of radiographs at the plurality of rotation angles and the plurality of linear stage positions, the second detector position being separated from the first detector position along either or both the translation axes by a distance less than a pixel size of the radiation detector;
  generate, based on radiographs in the first series of radiographs and corresponding radiographs in the second series of radiographs, a set of higher-resolution radiographs, wherein the higher-resolution radiographs have higher resolution than the radiographs in the first and second series of radiographs; and
  assemble the higher-resolution radiographs into a 3-dimensional radiograph of the sample.

2. The x-ray imaging system of claim 1, wherein the image acquisition system assembles the radiographs in an interlaced fashion to form the higher-resolution radiographs.

3. The x-ray imaging system of claim 1, further comprising:
  a first linear position encoder, wherein the first linear position encoder has a resolution finer than one-quarter of the pixel size of the radiation detector, wherein the first linear position encoder is configured to provide a direct measurement of displacement of the first translation stage; and
  a second linear position encoder, wherein the second linear position encoder has a resolution finer than one-quarter the pixel size of the radiation detector, wherein the second linear position encoder is configured to provide a direct measurement of displacement of the second translation stage,
  wherein the image acquisition system assembles radiographs of the first and second series of radiographs using the measurement of displacement of the first translation stage and the measurement of displacement of the second translation stage.

4. The x-ray imaging system of claim 1, wherein the x-ray generator generates x-rays with an energy range of 20 keV to 600 keV.

5. The x-ray imaging system of claim 1, wherein:
  the radiation detector comprises a flat-panel x-ray detector, and
  the pixel size of the radiation detector is in a range of 25 micrometers to 250 micrometers.

6. The x-ray imaging system of claim 1, wherein:
  the radiation detector comprises a lens-coupled detector, and
  the pixel size of the radiation detector is in a range of 0.1 micrometers to 10 micrometers.

7. An x-ray imaging system comprising:
  an x-ray generator configured to emit an x-ray beam;
  a two-dimensional pixelated area radiation detector having a plane arranged perpendicular to an emission direction of the x-ray beam, wherein a first translation stage and a second translation stage carry the radiation detector, wherein the first and second translation stages are configured to move the radiation detector along translation axes parallel to orientation directions of detector pixels of the radiation detector;
  a rotation stage having a rotation axis perpendicular to the emission direction of the x-ray beam, wherein the rotation stage is disposed between the x-ray generator and the radiation detector, wherein the rotation stage is configured to carry and rotate a sample;
  a linear stage configured to translate the sample linearly along an axis parallel to the rotation axis of the rotation stage, wherein a motion of the rotation stage and a motion of the linear stage are synchronized such that the x-ray beam traces a spiral pattern on the sample; and
  an image acquisition system configured to:
    acquire, while the radiation detector is at a first detector position, a first series of radiographs at a plurality of rotation angles of the rotation stage and a plurality of linear stage positions of the linear stage;
    after acquiring the first series of radiographs, acquire, while the radiation detector is at a second detector position, a second series of radiographs at the plurality of rotation angles and the plurality of linear stage positions, wherein the first detector position is separated from the second detector position along one or both the translation axes by a distance less than a linear size of the radiation detector along the respective translation axis;
    generate, based on radiographs in the first series of radiographs and corresponding radiographs in the second series of radiographs, a series of composite radiographs with larger fields of view; and
    assemble the generated series of composite radiographs into a 3-dimensional radiograph of the sample.

8. The x-ray imaging system of claim 7, further comprising:
  a first linear position encoder, wherein the first linear position encoder has a resolution finer than one-quarter of a pixel size of the radiation detector, wherein the first linear position encoder is configured to provide a direct measurement of displacement of the first translation stage;
  a second linear detector, wherein the second linear detector has a resolution finer than one-quarter the pixel size of the radiation detector, wherein the second linear detector is configured to provide a direct measurement of displacement of the second translation stage,
  wherein the image acquisition system is configured to generate the series of composite radiographs using the measurement of displacement of the first translation stage and the measurement of displacement of the second translation stage.

9. The x-ray imaging system of claim 7, wherein the x-ray generator generates x-rays with an energy range of 20 keV to 600 keV.

10. The x-ray imaging system of claim 7, wherein:
the radiation detector comprises a flat-panel x-ray detector, and
the pixel size of the radiation detector is in the range of 25 micrometers to 250 micrometers.

11. The x-ray imaging system of claim 7, wherein:
the radiation detector comprises a lens-coupled detector, and
the pixel size of the radiation detector is in the range of 0.1 micrometers to 10 micrometers.

12. The x-ray imaging system of claim 7, wherein the image acquisition system is further configured to use a cross-correlation algorithm to match edges of radiographs in the first and second series of radiographs prior to assembling the radiographs in the first and second series of radiographs into the series of composite radiographs.

13. The x-ray imaging system of claim 7, wherein the image acquisition system is further configured to use an interpolation algorithm to blend intensities of radiographs in the first and second series of radiographs prior to assembling the radiographs in the first and second series of radiographs into the series of composite radiographs.

14. A method comprising:
rotating a sample on a rotation stage having a rotation axis perpendicular to an emission direction of an x-ray beam emitted by an x-ray generator;
translating, on a linear stage, the sample linearly along an axis parallel to a rotation axis of the rotation stage, wherein a motion of the rotation stage and a motion of the linear stage are synchronized such that the x-ray beam traces a spiral pattern on the sample;
acquiring, while a radiation detector is at a first detector position, a first series of radiographs at a plurality of rotation angles of the rotation stage and a plurality of linear stage positions of the linear stage;
after acquiring the first series of radiographs, acquire, while the radiation detector is at a second detector position, a second series of radiographs at the plurality of rotation angles and the plurality of linear stage positions the second detector position being separated from the first detector position along either or both a first or a second translation axis parallel to orientation directions of detector pixels of the radiation detector, the first and second detector positions separated by a distance finer than a pixel size of the radiation detector, wherein a first translation stage and a second translation stage carry the radiation detector, wherein the first and second translation stages are configured to move the radiation detector along the first and second translation axes;
generating, based on radiographs in the first series of radiographs and corresponding radiographs in the second series of radiographs, a set of higher-resolution radiographs, wherein the higher-resolution radiographs have higher resolution than the radiographs in the first and second series of radiographs; and
assembling the higher-resolution radiographs into a 3-dimensional radiograph of the sample.

15. The method of claim 14, wherein assembling the radiographs comprises assembling the radiographs in an interlaced fashion to form the higher-resolution radiographs.

16. The method of claim 14, wherein:
a first linear position encoder has a resolution finer than one-quarter of the pixel size of the radiation detector and is configured to provide a direct measurement of displacement of the first translation stage, wherein a second linear position encoder has a resolution finer than one-quarter the pixel size of the radiation detector and is configured to provide a direct measurement of displacement of the second translation stage; and
generating the set of higher-resolution radiographs comprises assembling radiographs of the first and second series of radiographs using the measurement of displacement of the first translation stage and the measurement of displacement of the second translation stage.

17. The method of claim 14, wherein the x-ray generator generates x-rays with an energy range of 20 keV to 600 keV.

18. The method of claim 14, wherein:
the radiation detector comprises a flat-panel x-ray detector, and
the pixel size of the radiation detector is in a range of 25 micrometers to 250 micrometers.

19. The method of claim 14, wherein:
the radiation detector comprises a lens-coupled detector, and
the pixel size of the radiation detector is in a range of 0.1 micrometers to 10 micrometers.

20. A method comprising:
rotating a sample on a rotation stage having a rotation axis perpendicular to an emission direction of an x-ray beam emitted by an x-ray generator;
translating, on a linear stage, the sample linearly along an axis parallel to a rotation axis of the rotation stage, wherein a motion of the rotation stage and a motion of the linear stage are synchronized such that the x-ray beam traces a spiral pattern on the sample;
acquiring, while a radiation detector is at a first detector position, a first series of radiographs at a plurality of rotation angles of the rotation stage and a plurality of linear stage positions of the linear stage;
after acquiring the first series of radiographs, acquiring, while the radiation detector is at a second detector position, a second series of radiographs at the plurality of rotation angles and the plurality of linear stage positions, wherein the first and second detector positions are different detector positions along a first or a second translation axis parallel to orientation directions of detector pixels of the radiation detector, the first and second detector positions separated by a distance less than a linear size of the radiation detector along the first translation axis or the second translation axis, respectively,
wherein the radiation detector has a plane arranged perpendicular to an emission direction of the x-ray beam emitted by the x-ray generator, a first translation stage and a second translation stage carry the radiation detector, and the first and second translation stages are configured to move the radiation detector along the first and second translation axes;
generating, based on radiographs in the first series of radiographs and corresponding radiographs in the second series of radiographs, a series of composite radiographs with larger fields of view; and
assembling the generated series of composite radiographs into a 3-dimensional radiograph of the sample.

21. The method of claim 20, wherein:
a first linear position encoder has a resolution finer than one-quarter of the pixel size of the radiation detector and is configured to provide a direct measurement of displacement of the first translation stage, wherein a second linear position encoder has a resolution finer than one-quarter the pixel size of the radiation detector and is configured to provide a direct measurement of displacement of the second translation stage; and generating the series of composite radiographs comprises generating the series of composite radiographs using the measurement of displacement of the first translation stage and the measurement of displacement of the second translation stage.

22. The method of claim 20, wherein the x-ray generator generates x-rays with an energy range of 20 keV to 600 keV.

23. The method of claim 20, wherein:
the radiation detector comprises a flat-panel x-ray detector, and
the pixel size of the radiation detector is in the range of 25 micrometers to 250 micrometers.

24. The method of claim 20, wherein:
the radiation detector comprises a lens-coupled detector, and
the pixel size of the radiation detector is in the range of 0.1 micrometers to 10 micrometers.

25. The method of claim 20, further comprising using a cross-correlation algorithm to match edges of radiographs in the first and second series of radiographs prior to generating the series of composite radiographs.

26. The method of claim 20, further comprising using an interpolation algorithm to blend intensities of radiographs in the first and second series of radiographs prior to generating the series of composite radiographs.

27. A non-transitory computer-readable data storage medium having instructions stored thereon that, when executed, cause a computing system to:
rotate a sample on a rotation stage having a rotation axis perpendicular to an emission direction of an x-ray beam emitted by an x-ray generator;
translate, on a linear stage, the sample linearly along an axis parallel to a rotation axis of the rotation stage, wherein a motion of the rotation stage and a motion of the linear stage are synchronized such that the x-ray beam traces a spiral pattern on the sample;
acquire, while a radiation detector is at a first detector position, a first series of radiographs at a plurality of rotation angles of the rotation stage and a plurality linear stage positions of the linear stage;
after acquiring the first series of radiographs, acquire, while the radiation detector is at a second detector position, a second series of radiographs at the plurality of rotation angles of the rotation stage and the plurality of linear stage positions, the second detector position being separated from the first detector position along either or both first translation axis or a second translation axis parallel to orientation directions of detector pixels of the radiation detector, the first and second detector positions separated by a distance finer than a pixel size of the radiation detector, wherein a first translation stage and a second translation stage carry the radiation detector, wherein the first and second translation stages are configured to move the radiation detector along the first and second translation axes;
generate, based on radiographs in the first series of radiographs and corresponding radiographs in the second series of radiographs, a set of higher-resolution radiographs, wherein the higher-resolution radiographs have higher resolution than the radiographs in the first and second series of radiographs; and
assemble the higher-resolution radiographs into a 3-dimensional radiograph of the sample.

28. A non-transitory computer-readable data storage medium having instructions stored thereon that, when executed, cause a computing system to:
rotate a sample on a rotation stage having a rotation axis perpendicular to an emission direction of an x-ray beam emitted by an x-ray generator;
translate, on a linear stage, the sample linearly along an axis parallel to a rotation axis of the rotation stage, wherein a motion of the rotation stage and a motion of the linear stage are synchronized such that the x-ray beam traces a spiral pattern on the sample;
acquire, while a radiation detector is at a first detector position, a first series of radiographs at a plurality of rotation angles of the rotation stage and a plurality of linear stage positions of the linear stage;
after acquiring the first series of radiographs, acquire, while the radiation detector is at a second detector position, a second series of radiographs at the plurality of rotation angles and the plurality of linear stage positions, wherein the second detector position are different detector positions along a first translation axis or a second translation axis parallel to orientation directions of detector pixels of the radiation detector, the first and second detector positions separated by a distance less than a linear size of the radiation detector along the first translation axis or the second translation axis, respectively,
wherein the radiation detector has a plane arranged perpendicular to an emission direction of the x-ray beam emitted by the x-ray generator, a first translation stage and a second translation stage carry the radiation detector, and the first and second translation stages are configured to move the radiation detector along the first and second translation axes; and
generate, based on radiographs in the first series of radiographs and corresponding radiographs in the second series of radiographs, a series of composite radiographs with larger fields of view; and
assemble the generated series of composite radiographs into a 3-dimensional radiograph of the sample.

29. The x-ray imaging system of claim 1, wherein the image acquisition system is configured to use deconvolution to further improve resolution of the higher-resolution radiographs.

30. The method of claim 14, further comprising using deconvolution to further improve resolution of the higher-resolution radiographs.

31. The non-transitory computer-readable data storage medium of claim 27, wherein the instructions, when executed, further cause the computing system to use deconvolution to further improve resolution of the higher-resolution radiographs.

* * * * *